United States Patent
Yuki et al.

(10) Patent No.: US 9,612,112 B2
(45) Date of Patent: Apr. 4, 2017

(54) OPTICAL SYSTEM AND OPTICAL QUALITY MEASURING APPARATUS

(71) Applicant: CANON KABUSHIKI KAISHA, Tokyo (JP)

(72) Inventors: Hiroyuki Yuki, Utsunomiya (JP); Takashi Seki, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/630,950

(22) Filed: Feb. 25, 2015

(65) Prior Publication Data

US 2015/0247724 A1  Sep. 3, 2015

(30) Foreign Application Priority Data

Feb. 28, 2014  (JP) ................................. 2014-038060

(51) Int. Cl.
| | |
|---|---|
| *G01B 11/30* | (2006.01) |
| *G01N 21/55* | (2014.01) |
| *G01N 21/57* | (2006.01) |

(52) U.S. Cl.
CPC .......... *G01B 11/306* (2013.01); *G01B 11/303* (2013.01); *G01N 21/57* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS

| | | | |
|---|---|---|---|
| 3,997,268 A | 12/1976 | Fladda et al. | |
| 3,999,864 A | * 12/1976 | Mutter | ................... G01N 21/57 |
| | | | 250/227.29 |

(Continued)

FOREIGN PATENT DOCUMENTS

| | | |
|---|---|---|
| CN | 201819881 U | 5/2011 |
| GB | 1444780 A | 8/1976 |

(Continued)

OTHER PUBLICATIONS

European Search Report issued in application No. EP15156856.5, dated Jul. 21, 2015. Cited in U.S. related pending U.S. Appl. No. 14/632,438.

(Continued)

*Primary Examiner* — Tri Ton
*Assistant Examiner* — Jarreas C Underwood
(74) *Attorney, Agent, or Firm* — Rossi, Kimms & McDowell LLP

(57) ABSTRACT

An optical system comprising: a light source; a photodetector; a first light-receiving system for causing the photodetector to receive first reflected light with a first angle of reflection from a surface; and a second light-receiving system for causing the photodetector to receive second reflected light with a second angle of reflection, different from the first angle of reflection, from the surface is provided. Here, an incident area on the surface, in which light generating the first reflected light is incident, is spaced apart from an exiting area on the surface, which light, to be incident on the photodetector from the surface via the second light-receiving system, exits.

15 Claims, 3 Drawing Sheets

(52) U.S. Cl.
CPC ....... *G01N 21/55* (2013.01); *G01N 2201/061* (2013.01); *G01N 2201/068* (2013.01)

(56) References Cited

U.S. PATENT DOCUMENTS

| | | | | |
|---|---|---|---|---|
| 4,218,144 | A * | 8/1980 | Whitehouse | G01N 21/55 250/208.2 |
| 4,452,534 | A * | 6/1984 | Gribanov | G01B 11/2441 356/513 |
| 4,540,887 | A * | 9/1985 | Minerd | B41J 11/009 250/223 R |
| 4,914,309 | A * | 4/1990 | Masaharu | G01N 21/89 250/559.16 |
| 5,017,798 | A * | 5/1991 | Murakami | G01N 21/94 250/559.06 |
| 6,122,042 | A * | 9/2000 | Wunderman | A61B 1/05 356/343 |
| 6,215,552 | B1 * | 4/2001 | Acquaviva | G01B 11/0608 356/601 |
| 6,233,053 | B1 * | 5/2001 | Preston | G01N 21/57 356/429 |
| 6,249,341 | B1 | 6/2001 | Basiji et al. | |
| 6,292,576 | B1 * | 9/2001 | Brownlee | G06K 9/00013 340/5.83 |
| 6,428,171 | B1 | 8/2002 | Aoki et al. | |
| 6,509,964 | B2 * | 1/2003 | Wiles | G01N 21/57 356/237.2 |
| 6,600,167 | B2 * | 7/2003 | Sano | G01V 8/20 250/559.11 |
| 6,770,863 | B2 | 8/2004 | Walley | |
| 7,071,922 | B2 | 7/2006 | Sun et al. | |
| 7,391,518 | B1 | 6/2008 | Schwarz et al. | |
| 7,675,020 | B2 * | 3/2010 | Machida | G06F 3/0317 250/221 |
| 7,944,562 | B2 | 5/2011 | Schwarz | |
| 8,730,168 | B2 | 5/2014 | Moyer et al. | |
| 2002/0171826 | A1 | 11/2002 | Wiles et al. | |
| 2006/0109453 | A1 | 5/2006 | Swift et al. | |
| 2006/0227322 | A1 | 10/2006 | Kauffman et al. | |
| 2006/0243928 | A1 | 11/2006 | Blythe et al. | |
| 2007/0024870 | A1 | 2/2007 | Girard et al. | |
| 2009/0073203 | A1 | 3/2009 | Takekoshi et al. | |
| 2012/0167663 | A1 | 7/2012 | Groitzsch et al. | |

FOREIGN PATENT DOCUMENTS

| | | |
|---|---|---|
| JP | 2001041888 A | 2/2001 |
| JP | 2001264251 A | 9/2001 |
| WO | 2004097383 A1 | 11/2004 |

OTHER PUBLICATIONS

European Search Report issued in European counterpart application No. EP15156855.7, dated Jun. 24, 2015.

Office Action issued in U.S. Appl. No. 14/632,438 mailed Oct. 20, 2016.

Office Action issued in U.S. Appl. No. 14/632,438 mailed May 5, 2016.

\* cited by examiner

OPTICAL SYSTEM AND OPTICAL QUALITY MEASURING APPARATUS

BACKGROUND OF THE INVENTION

Field of the Invention

The present invention relates to an optical system and an optical quality measuring apparatus.

Description of the Related Art

Feeling of gloss (feeling of glossiness, optical quality) of an object such as printed matters, coatings, and plastic materials is an important factor for quality of the object. There have been conventionally various indexes according to characteristics of a surface to be detected serving as a concrete value representing the feeling of gloss, and measuring methods for the indexes. For example, these indexes comprise specular glossiness, haze and image clarity, spectral characteristics and the like. Japanese Patent Laid-Open No. 2001-41888 discloses a method for estimating and determining feeling of gloss by combining indexes measured by a plurality of mutually differing light-receiving angles in order to reduce difference between the glossiness serving as a value representing the feeling of gloss and the feeling of gloss actually felt by sight.

However, the method disclosed by Japanese Patent Laid-Open No. 2001-41888 uses photodetectors different from each other depending on each of the plurality of light-receiving angles. Therefore, the method disclosed by Japanese Patent Laid-Open No. 2001-41888 increases the provided number of the photodetectors by increasing the variation of the light-receiving angles in order to improve precision (accuracy) of the glossiness, and causes the configuration of an optical system to become complicated. In contrast, a conventional optical system exists in which the configuration is simplified by using the common photodetector to a plurality of measurements with the plurality of light-receiving angles. However, in the optical system using the shared photodetector, light irradiated at the measurement with one light-receiving angle can enter an optical path used in the measurement with another light-receiving angle to output a signal with noise by the photodetector.

SUMMARY OF THE INVENTION

The present invention provides, for example, an optical system advantageous in terms of simplification of a configuration thereof and accuracy of measurement thereby.

According to an aspect of the present invention, an optical system comprising: a light source; a photodetector; a first light-receiving system for causing the photodetector to receive first reflected light with a first angle of reflection from a surface; and a second light-receiving system for causing the photodetector to receive second reflected light with a second angle of reflection, different from the first angle of reflection, from the surface is provided, wherein an incident area on the surface, in which light generating the first reflected light is incident, is spaced apart from an exiting area on the surface, which light, to be incident on the photodetector from the surface via the second light-receiving system, exits.

Further features of the present invention will become apparent from the following description of exemplary embodiments (with reference to the attached drawings).

DESCRIPTION OF THE EMBODIMENTS

Hereinafter, preferred embodiments of the prevent invention are described with reference to the drawings.

First Embodiment

Figure 1A:
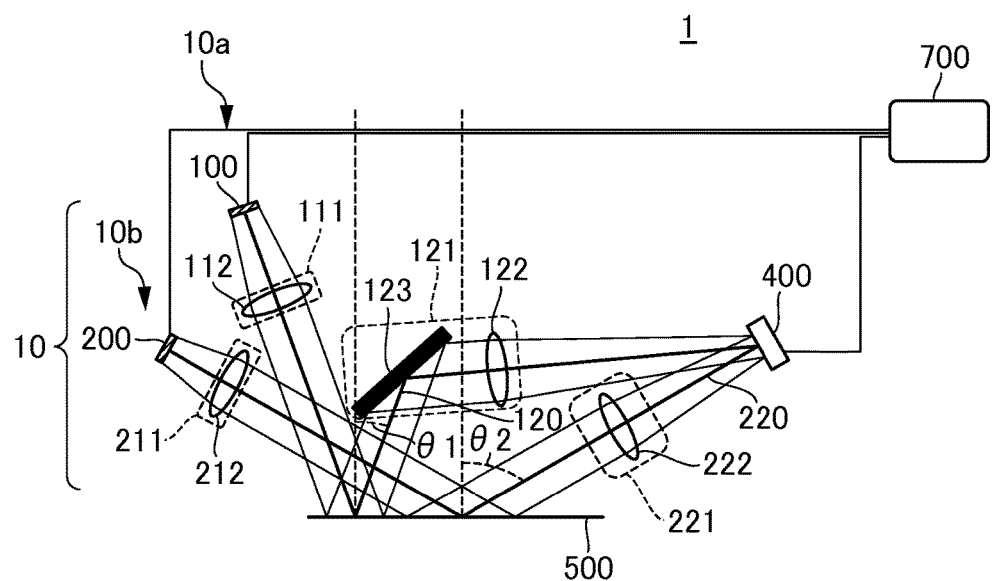
FIG. 1A illustrates a configuration of a glossmeter having an optical system according to a first embodiment of the present invention.
Figure 1B:
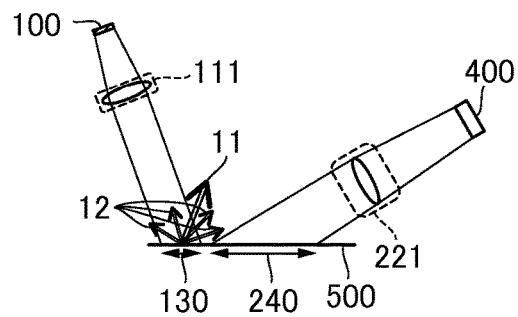
FIG. 1B illustrates a measurement state by a first optical system of the glossmeter as shown in FIG. 1A.
Figure 1C:
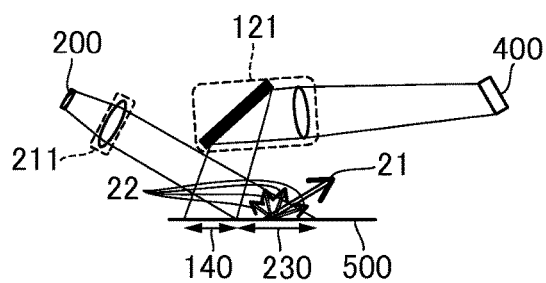
FIG. 1C illustrates a measurement state by a second optical system of the glossmeter as shown in FIG. 1A.

Firstly, a description will be given of an optical system according to a first embodiment of the present invention, and a glossmeter (an optical quality measuring apparatus) using the optical system. FIG. 1A to 1C are schematic diagrams of a glossmeter 1 that includes an optical system 10 according to the present embodiment. The glossmeter 1 measures glossiness of a surface of an object (also, referred to as a surface to be detected 500; a "subject surface" or a "surface") by using light. Hereinafter, the optical (visual) quality is referred to as "feeling of gloss (glossiness)", and an index representing the feeling of gloss such as specular glossiness, haze, or image clarity is referred to as "glossiness". For example, as an international standard, the specular glossiness is defined by the JIS-Z8741, and the haze is defined by the ASTM-E430, and the image clarity (DOI) is defined by the JIS-K7374 and the ASTM-D5767. Also, the international standard defines an aperture angle of a light source image (an aperture angle of a light-projecting system), an aperture angle of a photodetector (an aperture angle of a light-receiving system), an incident angle and a light-receiving angle as described in, for example, a fourth chapter "Measurement Conditions" in the JIS-Z8741. Therefore, in the present embodiment, sizes, configurations, and arrangements of a lens, a deflector, the photodetector and the like in the glossmeter 1 are set to satisfy a minimum basic condition described in the international standard. Note that this condition is not intended to limit the present invention, and the present invention may also be applied to the measurement of the glossiness with the originally defined aperture angle and the like. Thus, the glossmeter 1 adopts the optical system 10 with a plurality of light-receiving angles (angles of reflection) different from each other to more correctly comprehend the feeling of gloss. Here, the light-receiving angles have the same definition as that defined by the JIS-Z8741. Hereinafter, in the present embodiment, as an example, a description will be given of the optical system 10 comprising two optical systems in which two certain light-receiving angles are set to θ1 and θ2 (θ1<θ2).

FIG. 1A illustrates a configuration of the glossmeter 1. The glossmeter 1 comprises the optical system 10 and a control unit 700 (also, referred to as a "processing unit"). The optical system 10 includes a first optical system 10a and a second optical system 10b that set the respective receiving light angles so as to be different from each other. The first optical system 10a includes a first light source 100, a first light-projecting system 111, and a first light-receiving system 121. The second optical system 10b includes a second light source 200, a second light-projecting system 211, and a second light-receiving system 221. Here, the first light-receiving angle θ1 in the first optical system 10a (the first angle of reflection) is formed by the normal to the surface to be detected 500 and an optical axis 120 of the first light-receiving system 121. In contrast, the second light-receiving angle θ2 in the second optical system 10b (the second angle of reflection) is formed by the normal to the surface to be detected 500 and an optical axis 220 of the second light-receiving system 221. Furthermore, the optical system 10 includes a photodetector 400 able to receive the light from the two light-receiving systems of the first light-receiving system 121 and the second light-receiving system 221. In other words, the photodetectors that may be respectively included in the first optical system 10a and the second optical system 10b are shared as the single photodetector 400. In the present embodiment, each light-receiving angle θ1 and θ2 has various measuring items such as 20°, 45°, 60°, 75°, and 85° if the angles correspond to the international standard, and preferably, the angles are set depending on these measuring items and the like suitably.

Each light source 100 and 200 is arranged at a focal surface of each light-projecting system 111 and 211 respectively. Preferably, each light source 100 and 200 emits D65-type or C-type of standard light that is non-polarizing, and for example, white LED may be used, since it has less sequential drift and is inexpensive. Note that if the light source itself does not have the characteristics of the spectral distribution of the standard light such as the above examples, a colored glass filter may be arranged between the light source and the surface to be detected 500 to adjust the characteristics of the spectral distribution. Furthermore, while the first light source 100 and the second light source 200 are set as the light sources independent of each other in the present embodiment, the present invention is not limited thereto. For example, one illuminant (light source) is included in the optical system 10, and a beam splitter, a fiber coupler, or the like may be added to branch the light into a plurality of parts (two parts if these components corresponds to the present embodiment) to enable controlling the passing of the light by openable/closable openings.

The first light-projecting system 111 includes a collecting lens 112, and allows the light exiting from the first light source 100 to be collimated and to be incident to the surface to be detected 500, in order to generate the first reflected light. Also, the second light-projecting system 211 includes a collecting lens 212, and allows the light exiting from the second light source 200 to be collimated and to be incident to the surface to be detected 500, in order to generate the first reflected light. Note that although each light-projecting system 111 and 211 is set together with each collecting lens 112 and 212, the systems may include a plurality of lenses, the deflectors, and the like for the additional improvement of the performance and the alteration of the arrangement and the like. Also, while each light-projecting system 111 and 112 is configured to irradiate the collimate light in the present embodiment, they may be configured to collect or emit luminous flux to the surface to be detected 500. If the light source alone cannot deal with the adjustment of the light, a light-projecting side slit may be arranged to the first light source 100 or the second light source 200 as a secondary light source. Also, as shown in FIG. 1 of the JIS-Z8741, an intermediate image is provided and the intermediate imaging surface is set as a secondary light source surface. Thus, if the first light source 100 is arranged at the focal surface of the collecting lens 112, and in contrast, the second light source 200 is arranged in the focal surface of the collecting lens 212 to allow the collimate light to be entered to the surface to be detected 500, the arrangement conforms to the JIS-Z8741.

The first light-receiving system 121 includes a collecting lens 122, and allows regular reflected light (specular reflected light) in the first reflected light that is incident from the first light-projecting system 111 and then reflected on the surface to be detected 500 and the vicinity reflected light thereof, to be incident to the photodetector 400. Also, the first light-receiving system 121 includes a reflector 123 as a deflector that deflects the reflected light from the surface to be detected 500. Also, the second light-receiving system 221 includes a collecting lens 222, and allows the regular reflected light in the second reflected light that is incident from the second light-projecting system 211 and then reflected on the surface to be detected 500 and the vicinity reflected light thereof, to be incident to the photodetector 400. Note that a deflector, such as a prism, an eccentric lens, or a diffraction grating may be set as instead of the reflector 123, while the reflector 123 may be, for example, a mirror. Furthermore, although each light-receiving system 121 and 221 include each collecting lens 122, 222 in the present embodiment, the systems may include the plurality of lenses, the deflectors and the like for the additional improvement of the performance, and the alternation of the arrangement and the like.

The photodetector 400 is arranged at a focal position of each light-receiving system 121 and 122 or the position close to the focal positions (within the Rayleigh length). The photodetector 400 may adopt an imaging element (solid imaging element) such as, for example, a CCD or a CMOS. The use of such an imaging element has the advantage of being capable of picking up and processing the information about amount of the light of pixels corresponding to a slit in the following controller 700 without providing the opening shown in FIG. 1 of the JIS-Z8741 (light-receiving side slit S2). Also, the angle distribution of the reflected light can be acquired to calculate the haze defined in the ASTM-E430 or the image clarity defined in the ASTM-D5767 by the controller 700. In addition, if the imaging element is a colored type, the controller 700 can also acquire a signal depending on the hue to acquire spectrum information. Note that the photodetector 400 may be combined with the light-receiving side slit S2 as shown in the above JIS-Z8741. In this case, each light-receiving system 121 and 221 may include the light-receiving side slit S2.

Here, a relationship between the light-projecting system and the photodetector when the photodetector 400 can receive the regular reflected light in the light exiting from each light-projecting system 111 and 211 and then being reflected on the surface to be detected 500 is called a "relation (arrangement) of regular reflection". Thus, in the international standard, the relation of regular reflection is defined by the condition that the incident angle of the light-projecting system (the angle formed by the optical axis of the light-projecting system and the surface to be detected) is equal to the light-receiving angle of the photodetector. Accordingly, to satisfy this condition, there is the relation of regular reflection between the first light-projecting system 111 and the first light-receiving system 121, and also, there is the relation of regular reflection between the second light-projecting system 211 and the second light-receiving system 221.

The controller 700 is connected to each light source 100 and 200 and the photodetector 400 via electric wires. Additionally, the controller 700 allows either of the first light source 100 or the second light source 200 to emit the light in accordance with the measurement to acquire the glossiness based on the information (output) from the photodetector 400 (acquire the information about the glossiness). In this processing, the controller 700 controls the timing of the emitting of the light from the first light source 100 and the second light source 200, and the amount of the light, the irradiation time, and the like at each timing of the emitting of the light. Note that the concrete method for calculating the glossiness may be a method defined by the international standard (for example, the JIS-Z8741), or a method other than that defined by the international standard. The method other than that defined by the international standard comprises, for example, a method for acquiring a variable angle reflection distribution characteristic (spatial distributed characteristic of reflection) of the surface to be detected 500 by a measurement, and calculating the full width at one-half maximum value of this variable angle reflection distribution characteristic as the intensity of the vicinity light of the regular reflected light together with the intensity of the regular reflected light to calculate the glossiness based on these factors. Also, the method may comprise a method for irradiating the light to the surface to be detected 500 with an incident angle and acquiring an angle distribution function of the intensity of the scattered light by a measurement to calculate the glossiness based on the derivative value concerning the scattered angle of this function of the angle distribution.

Figure 4A:
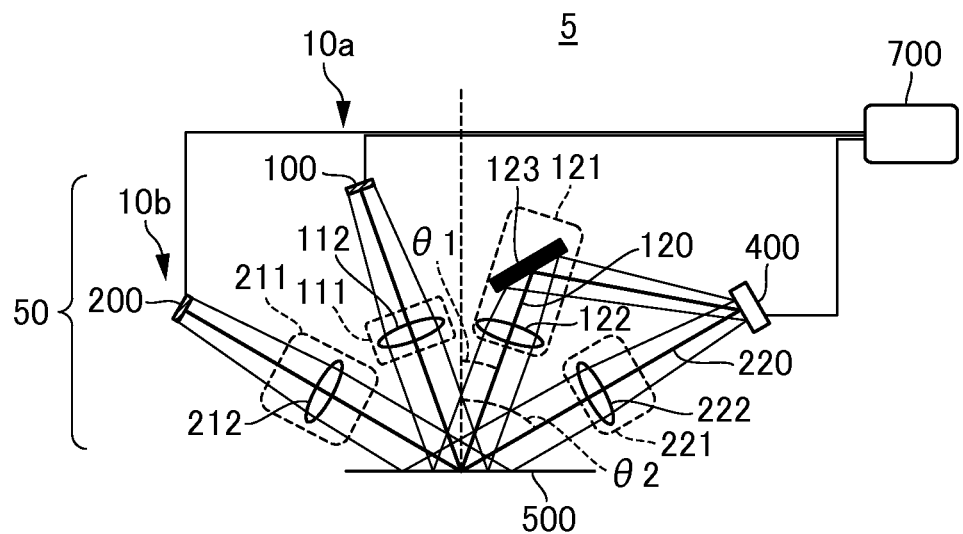
FIG. 4A illustrates a configuration of the glossmeter with a conventional optical system.
Figure 4B:
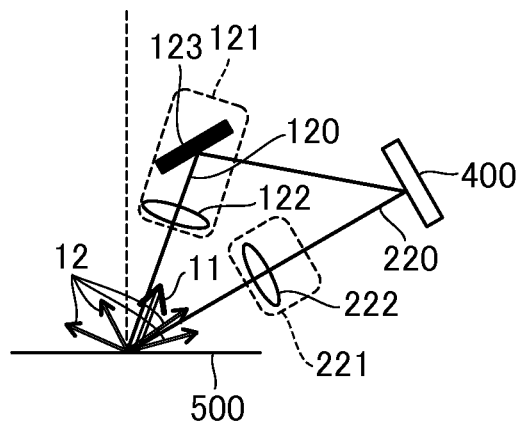
FIG. 4B illustrates a measurement state by the first optical system of the glossmeter as shown in FIG. 4A.
Figure 4C:
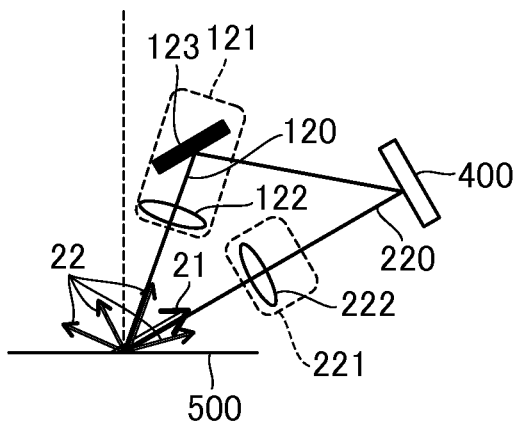
FIG. 4C illustrates a measurement state by the second optical system of the glossmeter as shown in FIG. 4A.

Next, a description will be given of a glossmeter with a conventional optical system as a comparison example to define the characteristics of the present embodiment. FIG. 4A to FIG. 4C are schematic diagrams illustrating a configuration of a glossmeter 5 that includes a conventional optical system 50. Note that in the optical system 50, components corresponding to those of the optical system 10 have the same reference numbers as those of the optical system 10 to simplify the comparison to the glossmeter 1 with the optical system 10 according to the present embodiment, and also a surface to be detected 500 and a controller 700 in the optical system 50 have same numbers as those in the glossmeter 1. Furthermore, the glossmeter 5 calculates the glossiness with two light-receiving angles θ1 and θ2 that different from each other, and the use of the photodetector 400 common to the both measurements are similar to those of the glossmeter 1 in the present embodiment.

FIG. 4A illustrates a configuration of the glossmeter 5. The first optical system 10a and the second optical system 10b in the optical system 50 have an identical measured area (area to be measured) on the surface to be detected 500 as shown in FIG. 4A, and the optical axis 120 of the first light-receiving system 121 have a position that is approximately identical to that of the optical axis 220 of the second light-receiving system 221 on the surface to be detected 500. FIG. 4B is a schematic diagram illustrating a state in which each light-receiving system 121 and 222 and the photodetector 400 are extracted from FIG. 4A, and the measurement is performed by the first optical system 10a. In this case, when the first light source 100 irradiates light to the surface to be detected 500, regular reflected light 11 and diffuse reflected light 12 is generated on the surface to be detected 500. The regular reflected light 11 and the vicinity reflected light thereof are irradiated to the photodetector 400 via the first light-receiving system 121. However, a portion of the diffuse reflected light 12 enters an optical path of the second optical system 10b that is different from the first optical system 10a, and is irradiated to the photodetector 400 via the second light-receiving system 221. Since the glossiness is calculated based on the received light information of the regular reflected light 11 and the vicinity reflected light thereof, the diffuse reflected light 12 received via the second light-receiving system 221 becomes noise, and can affect the calculated value.

In contrast, FIG. 4C is a schematic diagram illustrating a state in which each light-receiving system 121 and 221 and the photodetector 400 are extracted from FIG. 4A, and the measurement is performed by the second optical system 10b. In this case, when the second light source 200 irradiates light to the surface to be detected 500, regular reflected light 21 and diffuse reflected light 22 is generated on the surface to be detected 500. The regular reflected light 21 and the vicinity reflected light thereof are irradiated to the photodetector 400 via the second light-receiving system 221. However, a portion of the diffuse reflected light 22 enters the optical path of the first optical system 10a that is different from the second optical system 10b, and is irradiated to the photodetector 400 via the first light-receiving system 121. Thus, as described above, the diffuse reflected light 22 received via the first light-receiving system 121 becomes noise, and can affect the calculated value. Therefore, in the present embodiment, the optical system 10 is arranged as described below.

FIG. 1B is a schematic diagram illustrating a state in which the first light-projecting system 111, the second light-receiving system 221, and the photodetector 400 are extracted from FIG. 1A, and the measurement are performed by the first optical system 10a. Firstly, a first incident area 130 on the surface to be detected 500 (on the surface) is the maximum area on the surface to be detected 500, to which the first light-projecting system 111 can irradiate exiting light from the first light source 100 in the first optical system 10a at this processing. In other words, the exiting light from the first light source 100 is irradiated only to the first incident area 130 via the first light-projecting system 111, and not irradiated to the outside of the first incident area 130 via the first light-projecting system 111. The first incident area 130 is defined by the size of a light exiting unit of the first light source 100, the angular characteristics of the exiting light, the transmittable area of the first light-projecting system 111 that adjusted by the effective diameter, the outer diameter, and the like of the lens 112 constituting the first light-projecting system 111, and the like.

In contrast, in the second optical system 10b, a second exiting area 240 on the surface to be detected 500 is the maximum area that the second light-receiving system 221 can irradiate the reflected light in this processing to the photodetector 400. In other words, only the reflected light on the second exiting area 240 is irradiated to the photodetector 400 via the second light-receiving system 221, and the light reflected on the outside of the second exiting area 240 is not irradiated to the photodetector 400. The second exiting area 240 is defined by the size of a light receiving plane of the photodetector 400 (light-receivable area), the transmittable area of the second light-receiving system 221 that adjusted by the effective diameter, the outer diameter, and the like of the lens 222 constituting the second light-receiving system 221, and the like.

In addition, in the optical system 10, the first optical system 10a and the second optical system 10b are arranged such that the first incident area 130 and the second exiting area 240 are spaced apart from each other on the surface to be detected 500, as shown in FIG. 1B. Thereby, in the measurement using the first optical system 10a, irradiation of the diffuse reflected light 12 generated in the first incident area 130 to the light receiving plane of the photodetector 400 via the second light-receiving system 221 can be suppressed.

FIG. 1C is a schematic diagram illustrating a state in which the second light-projecting system 211, the first light-receiving system 121, and the photodetector 400 are extracted from FIG. 1A, and the measurement is performed by the second optical system 10b. Firstly, in the second optical system 10b at this processing, a second incident area 230 on the surface to be detected 500 is the maximum area on the surface to be detected 500 to which the second light-projecting system 211 can irradiate exiting light from the second light source 200. In other words, the exiting light from the second light source 200 is irradiated only to the second incident area 230 via the second light-projecting system 211 and is not irradiated to the outside of the second incident area 230 via the second light-projecting system 211. The second incident area 230 is defined by the size of a light exiting unit of the second light source 200, the angle characteristics of the exiting light, the transmittable area of the second light-projecting system adjusted by the effective diameter, the outer diameter, and the like of the lens 212 constituting the second light-projecting system 211, and the like.

In contrast, in the first optical system 10b, a first exiting area 140 on the surface to be detected 500 is the maximum area that the first light-receiving system 121 can irradiate the reflected light in this processing to the photodetector 400. In other words, only the reflected light in the first exiting area 140 is irradiated to the photodetector 400 via the first light-receiving system 121, and the light reflected on the outside of the first exiting area 140 is not irradiated to the photodetector 400. The first exiting area 140 is defined by the size of the light receiving plane of the photodetector 400, the transmittable area of the first light-receiving system 121 adjusted by the effective diameter, the outer diameter, and the like of the lens 122 constituting the first light-receiving system 121, and the like.

Additionally, in the optical system 10, the first optical system 10a and the second optical system 10b are arranged such that the second incident area 230 and the first exiting area 140 are spaced apart from each other on the surface to be detected 500, as shown in FIG. 1C. Thereby, in the measurement using the second optical system 10b, the irradiation of the diffuse reflected light 22 generated in the second incident area 230 to the light receiving plane of the photodetector 400 via the first light-receiving system 121 can be suppressed. Note that the present invention may include a lens-barrel and other components (for example, a shield) for shading the light, in order to define (set) the size of each area of the first incident area 130, the second incident area 230, the first exiting area 140, or the second exiting area 240, while these components are not shown.

Figure 2:
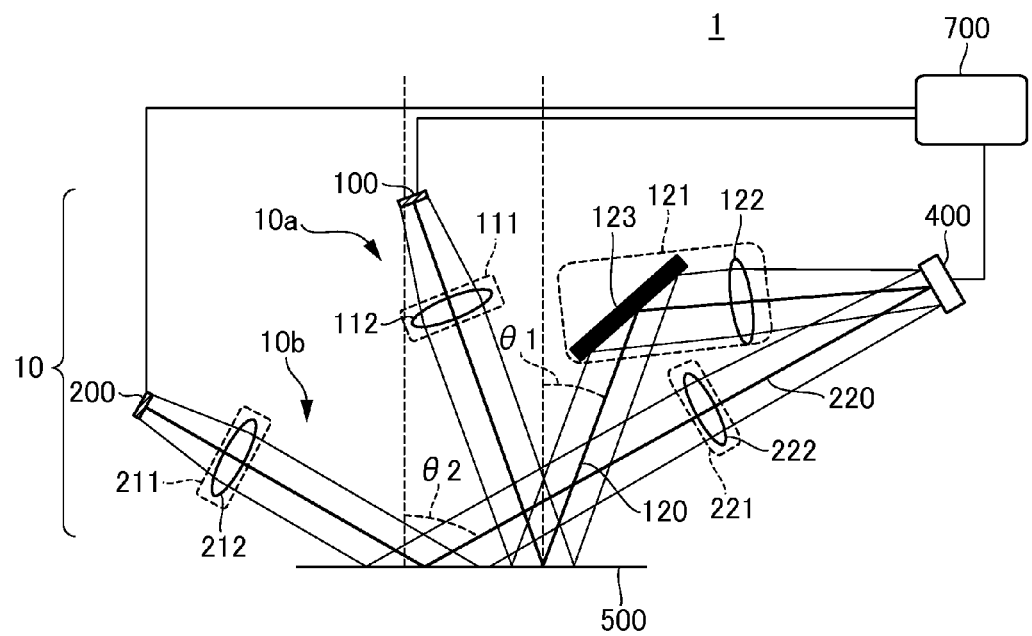
FIG. 2 illustrates a configuration of the glossmeter having the optical system according to the first embodiment of the present invention.

As described above, the optical system 10 uses the same photodetector 400 for the plurality of light-receiving angles θ1 and θ2, which are different from each other, to enable reducing the provided number of the photodetectors compared to the conventional technique using the dedicated photodetectors adapted to each of the plurality of light-receiving angles, that is, the configuration is simplified. Also, the optical system 10 is arranged as described above to enable reducing the noise that may be included in the information (output) of the photodetector 400, while responding to measurements with the plurality of light-receiving angles to improve the precision for the acquisition of the information. Note that the first optical system 10a is arranged more distant from the provided position of the photodetector 400 than the second optical system 10b in the above description. However, the configuration may be a configuration that is the reverse of the above configuration for the first optical system 10a and the second optical system 10b, as shown in FIG. 2.

As described above, the present embodiment can provide an optical system advantageous in terms of simplification of a configuration thereof and accuracy of measurement thereby. Also, the glossmeter using this optical system is advantageous for the simplicity of the configurations of the glossmeter itself. In addition, the glossmeter calculates the glossiness based on the information with reduced noise from the photodetector 400 (optical system 10) to improve the accuracy of the comprehension of the feeling of gloss by the measurement.

Second Embodiment

Figure 3:
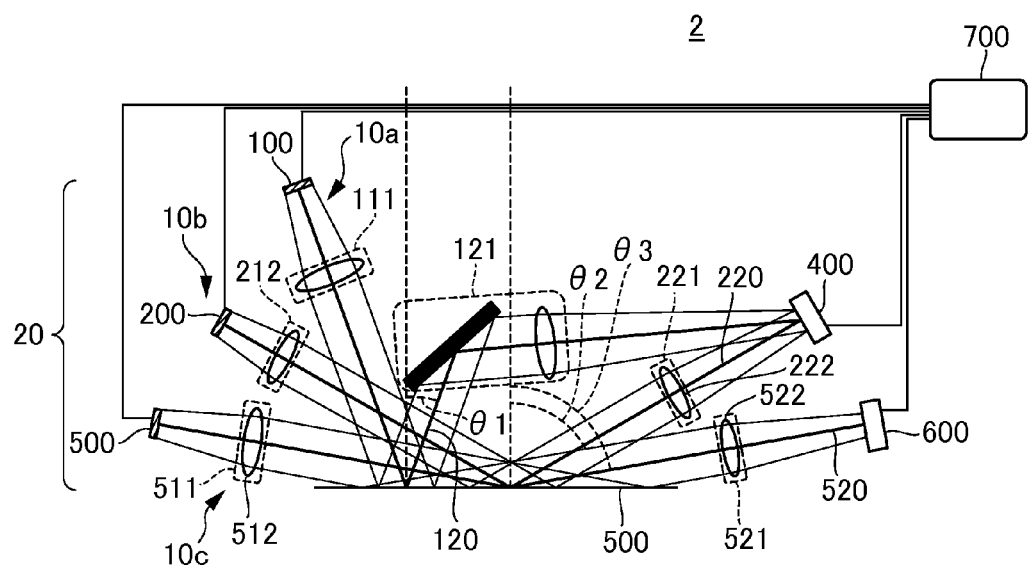
FIG. 3 illustrates a configuration of a glossmeter having an optical system according to a second embodiment of the present invention.

Next, a description will be given of an optical system according to a second embodiment, and a glossmeter using the optical system. FIG. 3 is a schematic diagram illustrating a configuration of a glossmeter 2 with an optical system 20 according to the present embodiment. In the first embodiment, the glossmeter 1 with the optical system 10 for performing measurement with the light-receiving angles θ1 and θ2, and the single photodetector 400 is described. On the other hand, the optical system 20 and the glossmeter 2 of the present embodiment includes a third optical system 10c with a third light-receiving angle (third angle) θ3 different from the first light-receiving angle θ1 and the second light-receiving angle θ2 in addition to each optical system 10a, 10b in the first embodiment. Note that components of the glossmeter 2 in the present embodiment that are the same as those of the glossmeter 1 have the same reference number as those of the glossmeter 1 in the first embodiment, and then the detailed description thereof will be omitted.

The third optical system 10c includes a third light source 500, a third light-projecting system 511, a third light-receiving system 521, and a second photodetector 600 different from the above photodetector 400. The third light source 500 is arranged in the focal surface of the third light-projecting system 511. The third light-projecting system 511 includes a collecting lens 512, and allows the light exited from the third light source 500 to be collimated and to be incident to the surface to be detected 500, in order to generate third reflected light. The third light-receiving system 521 includes a collecting lens 522, and allows the regular reflected light and the vicinity reflected light thereof in the third reflected light reflected on the surface to be detected 500 to be incident to the second photodetector 600. There is the relation of regular reflection between the third light-projecting system 511 and the third light-receiving system 521. The third light-receiving angle θ3 in the third optical system 10c is formed by the normal of the surface to be detected 500 and an optical axis 520 of the third light-receiving system 521. In the present embodiment, as an example, a start point of the optical axis 520 on the surface to be detected 500 is approximately same as a start point of the optical axis 220 on the surface to be detected 500 in the second optical system 10b, and each light-receiving angle has a relationship of θ1<θ2<θ3. Note that the third light-projecting system 511 or the third light-receiving system 521 may form a bent optical path by using the deflector to make the configuration compact. The second photodetector 600 is arranged at a focal position of the third light-receiving system 521 or the position close to the focal position. Note that similar types of each light source 100 and 200 and the photodetector 400 described in the first embodiment may be used as the third light source 500 and the second photodetector 600 respectively.

Here, in the optical system 20 according to the present embodiment, if the three light-receiving angles θ1 to θ3 are set as, for example, 20°, 60°, and 85° respectively in the optical system 30 according to the present embodiment, the angles conform to the ISO standard 2813, the ASTM-D523, and the JIS-Z8741. Alternatively, if the three light-receiving angles θ1 to θ3 are set as 20°, 45°, and 60° respectively, the angles conform to the ISO standard 7668, the ASTM-D2457, and the JIS-Z8741. Also, if any of the three light-receiving angles θ1 to θ3 is set as 75°, the angles conform to the JIS-Z8741 of the measurement standard of the glossiness, especially for the use of papers. Furthermore, to correctly comprehend the feeling of gloss, for example, if the third light-receiving angle θ3 is set in a direction different from the first light-receiving angle θ1 and the second light-receiving angle θ2 in the surface to be detected 500, the gloss anisotropy of the surface to be detected 500 can be measured.

As described above, the present embodiment can comprehend the feeling of gloss in more detail and measure other indices for glossiness, together with exhibiting the effect similar to the first embodiment. Note that although the optical system 20 according to the present embodiment comprises the three optical systems, the system may further add an optical system as the third optical system 10c, or may use a plurality of combinations made by the two optical systems constituting the optical system 10 of the first embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-038060 filed Feb. 28, 2014, which is hereby incorporated by reference herein in its entirety.

What is claimed is:

1. An optical system comprising:
    a photodetector;
    a first optical system for causing the photodetector to receive first reflected light with a first angle of reflection from a surface; and
    a second optical system for causing the photodetector to receive second reflected light with a second angle of reflection, different from the first angle of reflection, from the surface;
    wherein an incident area on the surface, in which light generating the first reflected light is incident, is spaced apart from an exiting area on the surface, which light, to be incident on the photodetector from the surface via the second optical system, exits, to reduce noise for one of the first reflected light and the second reflected light by the other of the first reflected light and the second reflected light.

2. The optical system according to claim 1, wherein an incident area on the surface, in which light generating the second reflected light is incident, is spaced apart from an exiting area on the surface, which light, to be incident on the photodetector from the surface via the first optical system, exits.

3. The optical system according to claim 1, further comprising:
    a first light-projecting system for generating the first reflected light and a second light-projecting system for generating the second reflected light,
    wherein the first optical system includes a deflector for deflecting the first reflected light toward the photodetector.

4. The optical system according to claim 3,
    wherein the first reflected light includes regular reflected light of light incident on the surface from the first light-projecting system,
    wherein the second reflected light includes regular reflected light of light incident on the surface from the second light-projecting system.

5. The optical system according to claim 1, further comprising:
    a second photodetector; and
    a third optical system for causing the second photodetector to receive third reflected light with a third angle of reflection, different from the first angle of reflection and the second angle of reflection, from the surface.

6. The optical system according to claim 5, further comprising:
    a third light-projecting system for generating the third reflected light;
    wherein the third reflected light includes regular reflected light of light incident on the surface from the third light-projecting system.

7. The optical system according to claim 1, wherein the first angle of reflection or the second angle of reflection is any one of 20°, 45°, 60°, 75° and 85°.

8. An apparatus for measuring optical quality of a surface, the apparatus comprising:
    an optical system comprising:
        a photodetector;
        a first optical system for causing the photodetector to receive first reflected light with a first angle of reflection from a surface;
        a second optical system for causing the photodetector to receive second reflected light with a second angle of reflection, different from the first angle of reflection, from the surface;
        a first light source configured to generate the first reflected light; and
        a second light source configured to generate the second reflected light,
        wherein an incident area on the surface, in which light generating the first reflected light is incident, is spaced apart from an exiting area on the surface, which light, to be incident on the photodetector from the surface via the second optical system, exits, to reduce noise for one of the first reflected light and the second reflected light by the other of the first reflected light and the second reflected light, and
        a controller connected to the photodetector, the first light source, and the second light source.

9. The apparatus according to claim 8, wherein the apparatus is configured to measure glossiness as the optical quality.

10. An optical system comprising:
    a first light-projecting system;
    a second light-projecting system;
    a photodetector;
    a first optical system for causing the photodetector to receive first reflected light reflected with a first angle of reflection on a surface, the first reflected light including specular reflected light of light incident on the surface from the first light-projecting system; and a second optical system for causing the photodetector to receive second reflected light reflected with a second angle of reflection, different from the first angle of reflection, on the surface, the second reflected light including specular reflected light of light incident on the surface from the second light-projecting system;

wherein an incident area on the surface, in which light generating the first reflected light is incident, is spaced apart from an exiting area on the surface, which light, to be incident on the photodetector from the surface via the second optical system, exits, to reduce noise for one of the first reflected light and the second reflected light by the other of the first reflected light and the second reflected light.

11. The optical system according to claim 10, wherein an incident area on the surface, in which light generating the second reflected light is incident, is spaced apart from an exiting area on the surface, which light, to be incident on the photodetector from the surface via the first optical system, exits.

12. The optical system according to claim 10, wherein the first optical system includes a deflector for deflecting the first reflected light toward the photodetector.

13. The optical system according to claim 10, further comprising:

a second photodetector; and a third optical system for causing the second photodetector to receive third reflected light with a third angle of reflection, different from the first angle of reflection and the second angle of reflection, from the surface.

14. The optical system according to claim 13, further comprising:

a third light-projecting system for generating the third reflected light;

wherein the third reflected light includes specular reflected light of light incident on the surface from the third light-projecting system.

15. The optical system according to claim 10, wherein the first angle of reflection or the second angle of reflection is any one of 20°, 45°, 60°, 75° and 85°.

* * * * *